United States Patent
Lihl et al.

(10) Patent No.: US 10,520,398 B2
(45) Date of Patent: Dec. 31, 2019

(54) MICROMANIPULATOR FOR A CRYOMICROTOME

(71) Applicant: Leica Mikrosysteme GmbH, Vienna (AT)

(72) Inventors: Reinhard Lihl, Vienna (AT); Michael Zimmermann, Leopoldsdorf (AT)

(73) Assignee: Leica Mikrosysteme GmbH (AT)

( * ) Notice: Subject to any disclaimer, the term of this patent is extended or adjusted under 35 U.S.C. 154(b) by 0 days.

(21) Appl. No.: 14/991,631

(22) Filed: Jan. 8, 2016

(65) Prior Publication Data

US 2016/0123847 A1    May 5, 2016

Related U.S. Application Data

(62) Division of application No. 12/337,193, filed on Dec. 17, 2008, now abandoned.

(30) Foreign Application Priority Data

Jan. 18, 2008    (AT) ........................ 75/2008

(51) Int. Cl.
  *G01N 1/06* (2006.01)
  *B26D 1/10* (2006.01)
  (Continued)

(52) U.S. Cl.
  CPC ............... *G01N 1/06* (2013.01); *B26D 1/00* (2013.01); *B26D 1/105* (2013.01); *G01N 1/42* (2013.01);
  (Continued)

(58) Field of Classification Search
  CPC ............... G01N 1/06; G01N 1/42; G01N 1/08
  (Continued)

(56) References Cited

U.S. PATENT DOCUMENTS 3,123,226 A    3/1964 Kulicke
3,377,898 A *  4/1968 Persson .................. G01N 1/06
                                           414/591
(Continued)

FOREIGN PATENT DOCUMENTS

AT    336920    6/1977
DE    1279368   10/1968
(Continued)

OTHER PUBLICATIONS

"Robotic grid loading system for a transmission electron microscope" by Clinton Potter et al. Jan. 22, 2004 (Year: 2004).*
(Continued)

*Primary Examiner* — Kenneth E Peterson
(74) *Attorney, Agent, or Firm* — Nelson Mullins Riley & Scarborough LLP

(57) ABSTRACT

A microtome system has a cryomicrotome with a sectioning device in which is provided a preparation holder and a knife edge that are guided past one another inside a working space during a sectioning operation, in order to produce thin sections of a preparation retained in the preparation holder. A micromanipulator is operable outside the working space. With the micromanipulator, a tool for retention of a specimen support is positioned proximate the knife edge during a sectioning operation in order to receive the sections that are produced, preferably for substantially stationary retention of the specimen support.

12 Claims, 3 Drawing Sheets

(51) Int. Cl.
*B26D 1/00* (2006.01)
*G01N 1/42* (2006.01)
*B26D 1/157* (2006.01)

(52) U.S. Cl.
CPC ........... *B26D 1/1575* (2013.01); *Y10T 83/222* (2015.04); *Y10T 83/283* (2015.04); *Y10T 83/6508* (2015.04); *Y10T 83/6571* (2015.04)

(58) Field of Classification Search
USPC ...................................................... 83/915.5
See application file for complete search history.

(56) References Cited

U.S. PATENT DOCUMENTS

| | | | |
|---|---|---|---|
| 3,723,226 A | 3/1973 | Pfohler | |
| 3,803,958 A * | 4/1974 | Fernandez-Moran | ... G01N 1/06 83/15 |
| 3,924,500 A | 12/1975 | Kindel | |
| 4,284,894 A | 8/1981 | Sitte et al. | |
| 4,907,158 A | 3/1990 | Kettler et al. | |
| 5,299,481 A | 4/1994 | Lihl et al. | |
| 5,348,883 A | 9/1994 | Togawa | |
| 5,761,977 A | 6/1998 | Jakobi et al. | |
| 5,776,298 A | 7/1998 | Franks | |
| 6,673,086 B1 | 1/2004 | Hofmeier et al. | |
| 7,005,294 B2 | 2/2006 | Lehmann | |
| 7,044,038 B2 | 5/2006 | Hess | |
| 7,393,629 B2 | 7/2008 | Fuhr et al. | |
| 7,704,741 B2 | 4/2010 | Fuhr et al. | |
| 8,001,878 B2 | 8/2011 | Lang et al. | |
| 8,074,547 B2 | 12/2011 | Ito et al. | |
| 2003/0021017 A1 | 1/2003 | Eijsackers et al. | |
| 2004/0209382 A1 | 10/2004 | Wakatsuki et al. | |
| 2006/0051735 A1 | 3/2006 | Fuhr et al. | |
| 2006/0134600 A1 | 6/2006 | Fuhr et al. | |
| 2006/0194309 A1 | 8/2006 | Fuhr et al. | |

FOREIGN PATENT DOCUMENTS

| | | |
|---|---|---|
| DE | 3718066 | 12/1988 |
| DE | 4307738 | 9/1993 |
| DE | 69210753 | 10/1996 |
| DE | 19932032 | 2/2001 |
| DE | 20221696 | 5/2007 |
| DE | 602004005524 | 12/2007 |
| EP | 0577084 | 1/1994 |
| EP | 1811280 | 7/2007 |
| EP | 1826547 | 8/2007 |
| GB | 1518792 | 7/1978 |
| GB | 2110838 * | 6/1983 |
| JP | 2006329733 | 12/2006 |
| WO | 2003107066 | 12/2003 |
| WO | 2004074424 | 9/2004 |
| WO | 2006036771 | 4/2006 |

OTHER PUBLICATIONS

Ladinsky, Mark S., et al. "Vitreous Cryo-Sectioning of Cells Facilitated by a Micromanipulator," Journal of Microscopy, vol. 224, Nov. 2, 2006, pp. 129-134.
Examination Report from Austrian Patent Office dated Oct. 22, 2008.
German Examination Report dated Nov. 27, 2008.
Final Office Action dated Mar. 14, 2016, from corresponding U.S. Appl. No. 12/337,193.

* cited by examiner

MICROMANIPULATOR FOR A CRYOMICROTOME

The present application is a division of U.S. application Ser. No. 12/337,193, filed Dec. 17, 2008 now abandoned, which claims the benefit of Austrian Patent Application No. AT 75/2008, filed Jan. 18, 2008, the entire disclosure of each of which are hereby incorporated by reference herein.

The invention relates to a microtome, in particular a cryomicrotome, having a sectioning device in which are provided a preparation holder and a knife edge that are guided past one another inside a working space during a sectioning operation, in order to produce thin sections of a preparation retained in the preparation holder.

BACKGROUND

The production of thin sections of cryopreserved specimens, in particular biological specimens with vitrified material (i.e. solidified in glassy fashion), is important for cryo-electron microscopy and similar investigation methods. Cryopreserved specimens largely avoid distortions that can derive from desiccation, chemical modifications (including contrast agents), and other specimen stabilization methods and therefore enable investigation of the specimen at the ultrastructure scale in a state that comes very close to the living state of the initial specimen. A very thin section thickness is required for investigation using an electron microscope or the like, however, namely tens to a few hundred nanometers depending on the type of specimen. This, along with the deep-frozen state (generally below $-100°$ C.) of the sections, places serious demands on the user's skill and on the quality and precision of the sectioning device.

In addition to the actual sectioning operation, removing the sections from the edge of the knife and applying them onto a specimen carrier (referred to here as a specimen support) constitutes a particularly delicate operation. The specimen supports used for an electron microscope are generally grids made of a thin metal foil. For room-temperature applications the possibility exists, for example, of carrying the sections away from the edge on the surface of a water bath in which the sectioning apparatus is partly immersed; this offers the additional advantage that sections crimped during the sectioning operation can relax again (decompress) on the water surface, and are only then received by the grid. The water-bath approach is not available for low-temperature applications, and transport from the knife edge to the grid must therefore be effected in some other manner.

Because manipulation of sections in a cooled preparation chamber of an ultramicrotome is performed manually, especially during the sectioning operation, such manipulation requires an experienced user. Because the sections are produced in a sequence of many sectioning motions rather than individually, the sections are produced in the form of an interconnected strip of a plurality of individual sections. An interconnected strip of this kind is then pulled with a suitable tool, for example a hair mounted at the end of a wooden rod, from the knife edge over a grid and then immediately laid down. Accurate positioning of the grid with respect to the knife blade is necessary so that the fragile section strip can be picked up close to the knife edge.

A known device for producing low-temperature thin sections is the Leica EM FC6, available from the assignee of the present application, Leica Microsystems, GmbH, of Hernalser Hauptstrasse 219, A-1170 Vienna, Austria. The sectioning operation takes place in a working space with at least one side wall that is adjacent or thermally coupled to a cooling chamber Tillable with a coolant (e.g. liquid nitrogen), or where the working space is surrounded on several sides (e.g. in cupped fashion) by the cooling chamber. The working space cooled in this fashion is open toward the top and thus accessible to the user. The specimen to be sectioned is mounted on a specimen holder positioned on one vertical side of the working space, to which holder a vertical motion can be imparted in the manner of a vibrating head. The sectioning knife is unmoved during the sectioning operation and is positioned by means of a knife holder mounted in the floor of the working space (shifting for alignment purposes is possible). The knife holder furthermore contains instruments for retaining a grid (or a few grids), in particular a grid holder into which the grid can be clamped at its edge. This grid holder is shiftable in a horizontal direction toward and away from the knife; positioning consists solely in sliding toward the knife. An end stop prevents contact between the grid and the knife. The specimen preparation device located in the working space can furthermore comprise an apparatus having a preparation surface, in which grids are set in place and pressed while still in the working space. Placement of the grid onto a preparation surface of this kind, in particular the operation of pressing the sections onto the grid (specimen support), can, however, generate contaminants.

In order to counteract electrostatic charging of the sections in the cooled working space, the Leica EM FC6 provides an ionizer that slightly ionizes the gases (vapors) surrounding the material to be sectioned, in order to ensure dissipation of electrical charges.

With other, earlier models, holders for multiple specimen supports were provided. These holders had a coarse vertical displacement capability, and (by shifting) a coarse displacement capability in the horizontal plane. These models, as well, comprised a section press integrated into the specimen preparation device.

The aforesaid known devices have the following disadvantages:

Guidance of the section strip and positioning of the grid are performed manually, and are thus susceptible to operating errors, and require considerable user skill.

The numerous manipulation steps on the sections within the working space are laborious and can result in section losses and contamination.

The grid is retained on the side facing the knife edge. This impedes placement of the section strip, since the section strip is pulled from the knife edge toward the holder.

The effect of the ionizer is impaired by components made of solid metal for retaining the grid.

There is a risk of contaminating the sections with condensed ice or other contaminants from the environment as a result of manipulation that lasts too long.

The article "Vitreous cryo-sectioning of cells facilitated by a micromanipulator," by M. Ladinsky et al., J. Microsc. 224 (2006) 129-134 describes a cryomicrotome arrangement having a micromanipulator. In it, a fiber retained by the micromanipulator at the end of a wooden rod serves to pick up the sections and guide the section strip to the support. The manipulator is mounted on the equipment table, not on the cooling chamber itself. Because a vibration damping system is present between the equipment table and cooling chamber, relative motions occur between the manipulator and the ultramicrotome with cooling chamber; in particular, contact by the user (e.g. operation of the microtome arrangement's stereomicroscope) inevitably causes such relative motions.

DE 202 21 696 U1 describes a microscope arrangement having a micromanipulator for carrying out microscopic manipulations and injections on living material. The micromanipulator is attached to the microscope by means of an adapter. DE 1279 368 A describes a micromanipulator for moving and producing small tools under a microscope, the micromanipulator being arranged, by means of a magnetic tool holder, at the lower objective end of the microscope.

SUMMARY OF THE INVENTION

Accordingly, one object of one or more embodiments of the invention is to improve the manipulation of sections immediately after the sectioning operation. In particular, sources of error in the context of manual handling are to be precluded.

This and other objects may be achieved by a microtome, in particular a cryomicrotome, having a micromanipulator with which, according to the present invention, a tool for retaining a specimen support that is provided for reception of the sections that are produced is positionable proximate the knife edge during a sectioning operation, the micromanipulator being operable outside the working space.

The micromanipulator according to the present invention enables substantially improved, precise positioning of the specimen holder during the operation of loading the specimen holder with the sections. A further advantage of an embodiment of the present invention described herein is that a grid loaded with sections can be laid into a transfer container without having to perform a removal of the retaining tool from the micromanipulator, by way of a positioning motion of the manipulator.

With regard to the numerous manipulation steps involving the sections inside the working space (position specimen and knife before cutting, pick up and position grid with holder, place section strip on grid, open grid holder, transfer to grid press, manually pick up grid with forceps and load into a transfer container), an embodiment of the invention described herein thus results in a definite simplification and in more expeditious execution of the procedure when manufacturing preparation sections, thus also reducing the risk of section losses and contamination.

The procedure that can be carried out with the device according to such embodiment of the present invention is not only simpler but also substantially faster than with conventional units. The tool, e.g. a forceps, can be loaded with a prepared grid and, shortly before sectioning begins, installed into the micromanipulator and positioned into the working chamber.

A further advantage of such embodiment is that influence on the ionizer is reduced. The tool retained by the manipulator projects only with its tip into the working space. In particular, a forceps having thin tips, or even a ceramic coating or ceramic tips, can minimize the negative influence on ionizer effectiveness. This yields a considerable improvement over known devices, in which complex apparatuses having large metallic surfaces are housed in the working space.

In accordance with the invention, the micromanipulator is used to position the specimen support (instead of picking up the sections or the section strip and delivering them/it to the specimen support). Once the specimen support has been loaded with sections, the arrangement according to an embodiment of the present invention particularly described herein allows the specimen support to be placed in a transfer container without removing the forceps from the holder by way of the positioning motion of the manipulator. In this regard, the micromanipulator is preferably set up for substantially stationary retention of the specimen support.

A preferred embodiment of the invention refers to a cryomicrotome having a cooling chamber that surrounds the working space but permits the user access to the working space, for example through an opening (or several) that preferably allows access from above, the micromanipulator engaging through the opening (or one of the openings) and being operable from outside the cooling chamber. It is favorable in this context, in order to exclude shocks that could lead to a relative motion between the tool retained by the micromanipulator and the material being sectioned in the working area, if the micromanipulator is mounted on the cooling chamber.

For similar reasons, it can be advantageous to connect the micromanipulator fixedly to the microtome (e.g. on its housing or on another load-bearing component).

In order to improve adjustment capabilities for different specimen sizes, and for simplified transport of the specimen support to the transfer container, one preferred embodiment of the micromanipulator comprises a three-axis positioning device.

In a preferred refinement of the invention, the micromanipulator comprises a receptacle for a forceps. A forceps whose tip is bent can be provided, in order to retain the specimen support almost parallel to the knife edge. The angle of this bend is, usefully, the angle at which the longitudinal axis is tilted with respect to the feed direction of the knife edge.

Provision can further be made that an elongated tool retained in the micromanipulator is rotatable about its longitudinal axis. This results in more-flexible handling of the specimen support, which can be advantageous for placement of the grid. In addition, it permits easier handling of the specimen holder upon transport into a transfer container.

In addition, a transfer container that comprises at least one receiving opening for specimen supports can be replaceably insertable in the working space. In this case, it is advantageous if the range of motion of the micromanipulator is sufficient to move a specimen support retained thereby to the location of the receiving opening(s) of an inserted transfer container.

Lastly, the fact that one or more axes of motion of the micromanipulator are motorized can represent an additional improvement in operating convenience, in an embodiment of the present invention.

BRIEF DESCRIPTION OF THE DRAWINGS

The invention, together with further advantages, is explained in greater detail below with reference to a non-limiting exemplifying embodiment that is depicted in the appended drawings, in which.

Figure 1:
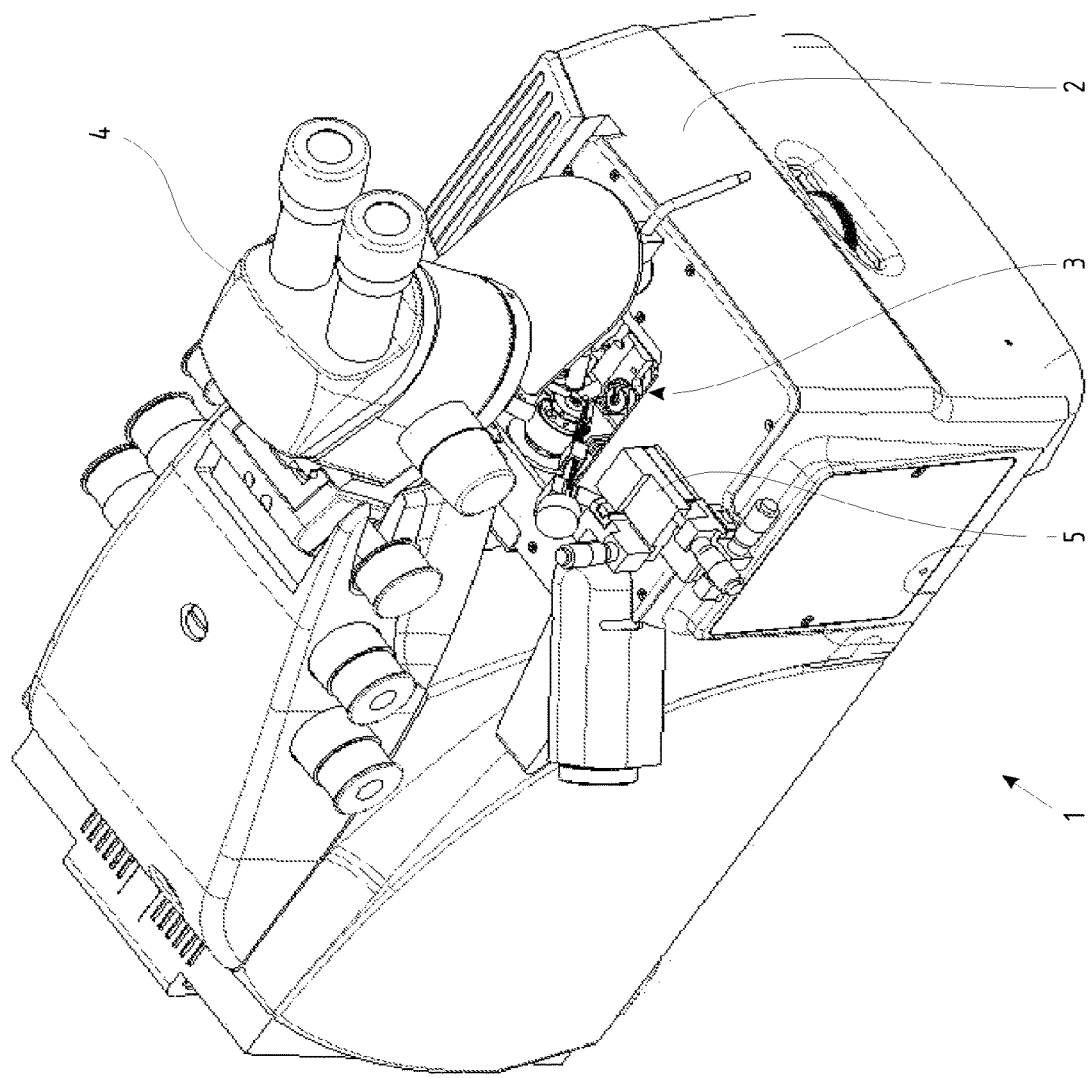
FIG. 1 is a perspective view of an ultramicrotome having a manipulator according to an embodiment of the invention.

Repeat use of reference characters in the present specification and drawings is intended to represent same or analogous features or elements of one or more embodiments of the invention.

DETAILED DESCRIPTION

Reference will be made in detail to one or more embodiments of the present invention, one or more examples of which are illustrated in the accompanying drawings.

FIG. 1 shows an ultramicrotome 1 that is based on the above-described Leica EM FC6 and, in a manner known with regard to that device, comprises a cooling chamber 2 having a working chamber 3 surrounded by the cooling chamber, in which the tools for the production of sections are housed. A stereomicroscope 4 serves, in a manner also known, for observing the preparation and the sections during sectioning and subsequent manipulation. In a departure from known devices, a manipulator 5 is installed on one side of the cooling chamber. As a rule, manipulator 5 is located on the left side in order to enable manual manipulation of the specimens from the right side of the device, although installation on the right side is, of course, also possible (especially for left-handers).

Figure 2:
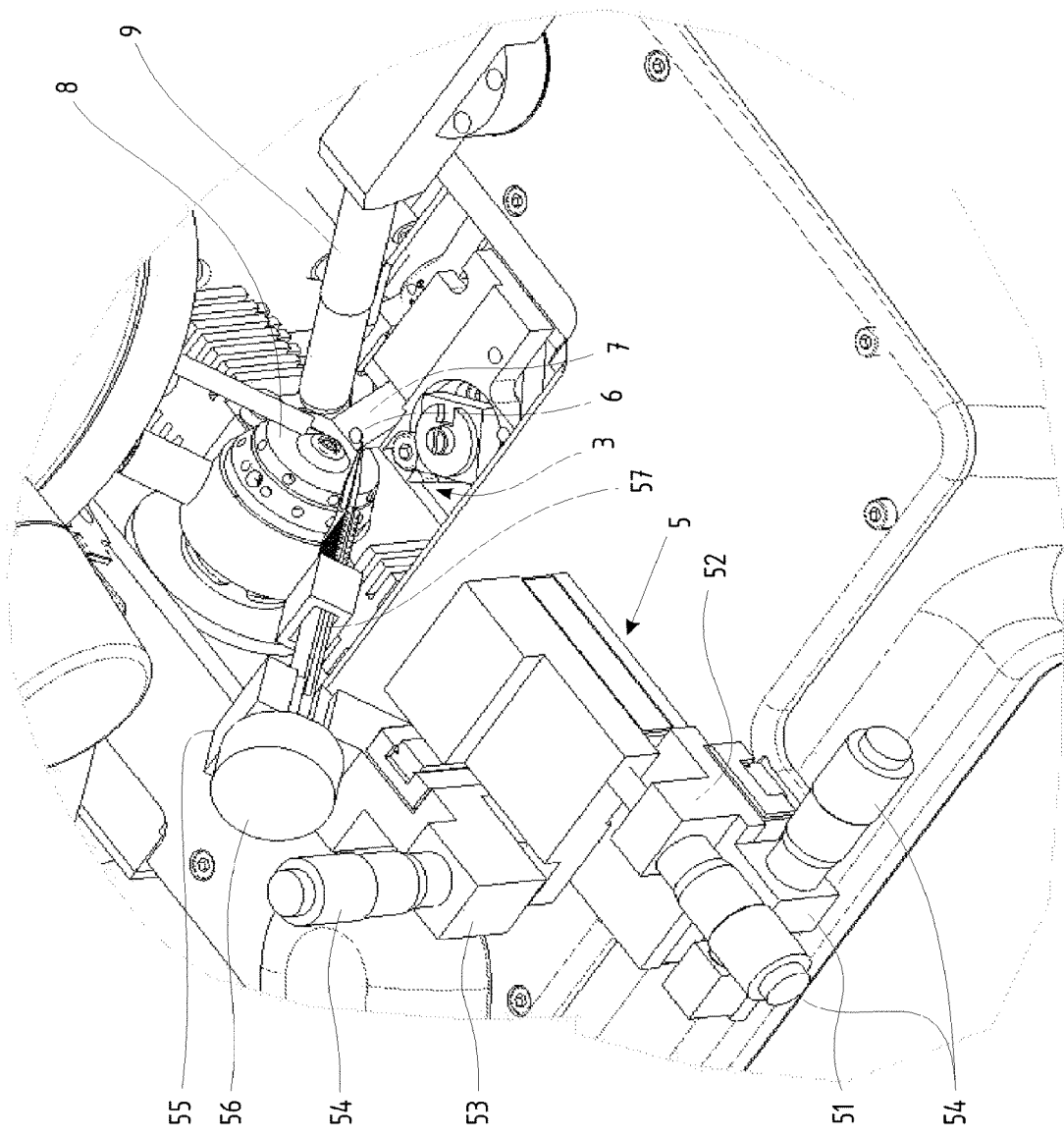
FIG. 2 is a detail of FIG. 1 showing the manipulator and the working space of the ultramicrotome.

Manipulator 5 is shown in further detail in FIG. 2. Manipulator 5, constituting a micromanipulator, possesses displacement capabilities 51, 52, 53 in three axes, namely 51 and 52 for horizontal motion and 53 for vertical displacement. Each axis is made up of a linear guide and a micrometer screw as displacement element. Displacement elements 54 can also be embodied in motorized fashion by means of a precision stepping motor. All these displacement motions act on a manipulator body 55. Located therein is a receptacle 56 for a tool 57 that can be, for example, a forceps. Receptacle 56 is additionally rotatable about the longitudinal axis of tool 57. With the aid of the manipulator, a grid 6 retained in tool 57 can be positioned proximate a knife 7 and of the preparation (not shown) retained in sectioning head 8. An ionizer 9, which is preferably directed toward the edge of knife 7, can additionally be provided.

Figure 3:
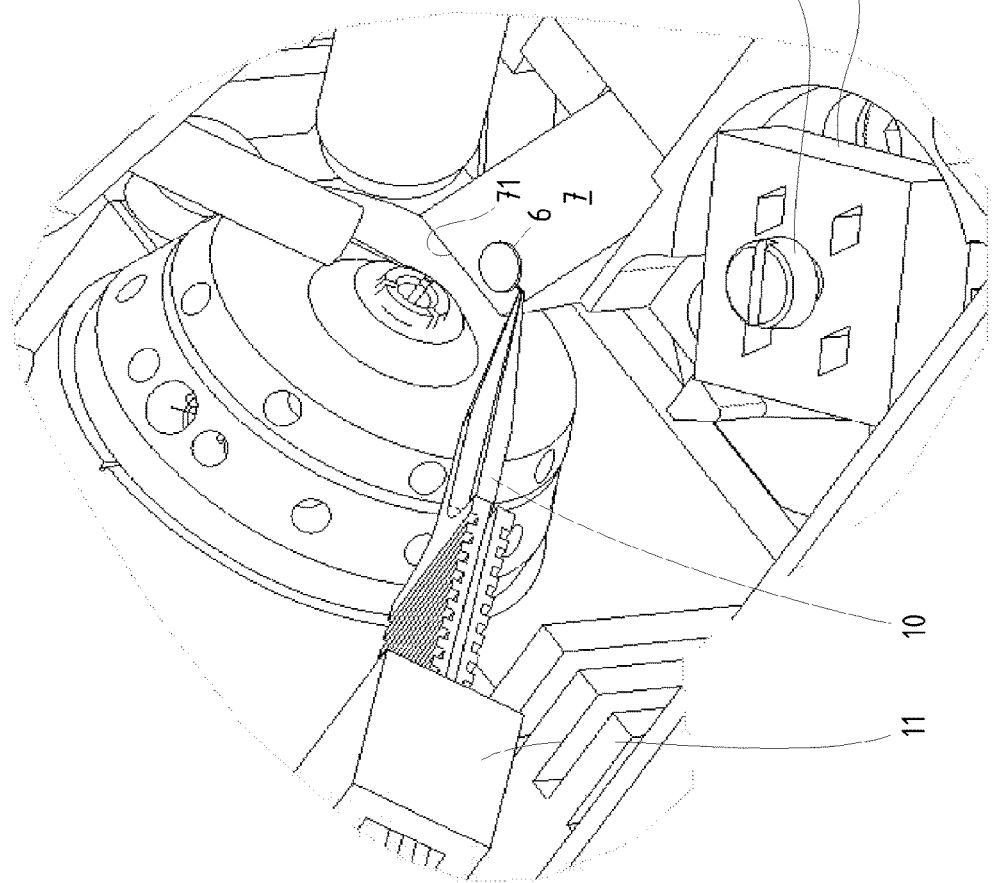

FIG. 3 shows, in a detail of FIG. 2, the manipulation of forceps 10 and of a grid 6 serving as a specimen support. The forceps can preferably be equipped with a slide 11 for immobilizing the forceps tips when clamping a grid 6. Forceps 10 is bent near the tip at an angle of approximately 45°, enabling grid 6 to be positioned parallel to knife edge 71. This arrangement is very well suited for placement of the section strip onto grid 6.

The arrangement of manipulator 5 and forceps 10 on one side (in this case the left side) of the device advantageously allows the user to access the working space from the other side (in this case from the right). The user can thus intervene manually during the sectioning operation, in particular in order to remove from knife blade 71—for example, by means of a fiber (e.g. hair) retained at the end of a stick or another holder—the section strip that is produced, and guide it to a desired destination, in this case grid 6 prepared as a specimen carrier or support. During this operation, grid 6 remains substantially stationary, since the positioning of grid is set by means of the manipulator before the sectioning operation and then remains the same except for any slight position corrections (realignments).

After deposition of the section strip (not shown) onto grid 6, the latter needs to be brought into a transfer container. This operation can likewise be carried out with manipulator 5 according to the presently-described embodiment of the present invention without removing the forceps from its holder.

Figure 4:
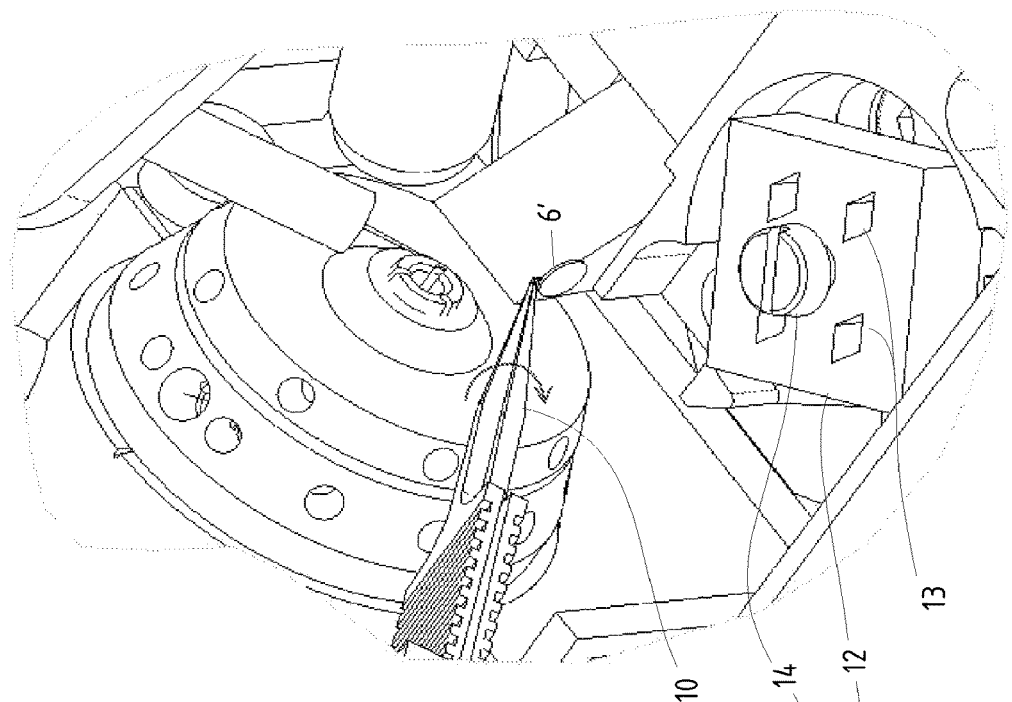
FIGS. 3 and 4 are enlarged details of FIG. 2 of the working space, respectively showing the retained tool with a specimen support in two different positions, namely during the pickup of sections (FIG. 3) and upon introduction of the specimen support into a transfer container (FIG. 4).

FIG. 4 illustrates introduction into the transfer container, in a depiction corresponding to FIG. 3.

A transfer container 12 can be inserted, as shown, at the bottom of working space 3, for example alongside knife 7 or alongside the vertical plane constituted by the cutting head and knife. The transfer container comprises a number of openings 13, e.g. four openings, which have, e.g., a diamond-shaped conformation into which a grid can be inserted along the long diagonal. Transfer container 12 can be secured, for example by means of a screw 14, in a suitable orientation in which openings 13 advantageously extend with their long diagonal parallel to the aforesaid vertical plane.

After deposition of the sectioned material, the forceps is rotated about its longitudinal axis by rotating receptacle 56 (FIG. 2) 180°, with the result that grid 6 assumes a vertical position and points vertically downward. By displacement via the three axes of the manipulator, the grid can now be brought into one of the openings 13 of container 12 and deposited there by an opening operation using slide 11. Transfer container 12 having the grid is closed off with a cover (FIG. 2) and taken out of the chamber.

After deposition of the grid into the transfer container, forceps 10 is removed from receptacle 56 (FIG. 2) and can be loaded, outside the device, with a new grid for a further sectioning operation.

While one or more embodiments of the present invention have been described above, it should be understood that any and all equivalent realizations of the present invention are included within the scope and spirit thereof. Thus, the embodiments presented herein are provided by way of example only.

What is claimed is:

1. A method of operating a microtome system having
   a cryomicrotome with a working space and a sectioning device comprised of a preparation holder and a knife edge,
   a micromanipulator,
   a tool for retaining a specimen support, and
   a transfer container that comprises at least one receiving opening for a said specimen support and that is replaceably insertable in the working space,
   wherein a portion of the micromanipulator that controls position of the tool is located outside the working space,
   comprising the steps of:
     retaining a preparation by the preparation holder;
     in a sectioning operation, guiding the preparation holder and the knife edge past one another inside the working space to thereby produce thin sections of the preparation; and
     before the sectioning operation, positioning the tool by the micromanipulator to a position at which the tool retains the specimen support proximate the knife edge; and
     maintaining, solely by the micromanipulator and the tool, the specimen support proximate the knife edge and substantially stationary during the sectioning operation and loading of a thin section of the preparation produced by the sectioning operation from the knife edge onto the specimen support.

2. The method as in claim 1, wherein the micromanipulator comprises a receptacle, and the tool comprises a forceps received by the receptacle.

3. The method as in claim 2, wherein the forceps is elongated and has a tip that is bent with respect to a longitudinal dimension of the forceps.

4. The method as in claim 3, wherein the positioning step comprises retaining the tool in the micromanipulator so that the forceps is rotatable about an axis along the longitudinal dimension.

5. The method as in claim 1, further comprising the step of, following the maintaining step and when the transfer container is disposed in the working space, controlling the tool by the micromanipulator to deposit the specimen support in a said receiving opening.

6. The method as in claim 5, further comprising the steps of, following the controlling step, removing the tool from the working space and securing a second said specimen support by the tool outside the working space.

7. A method of operating a microtome system having
a cryomicrotome with a working space and a sectioning device comprised of a preparation holder and a knife edge,
a micromanipulator,
a tool for retaining a specimen support, and
a transfer container that comprises at least one receiving opening for a said specimen support and that is replaceably insertable in the working space,
wherein a portion of the micromanipulator that controls position of the tool is located outside the working space,
comprising the steps of:
retaining a preparation by the preparation holder;
in a sectioning operation, guiding the preparation holder and the knife edge past one another inside the working space to thereby produce thin sections of the preparation; and
before the sectioning operation, positioning the tool by the micromanipulator to a position at which the tool retains the specimen support proximate the knife edge;
after the sectioning operation, loading a thin section of the preparation produced by the sectioning operation from the knife edge onto the specimen support without receiving the thin section into a liquid bath; and
maintaining, solely by the micromanipulator and the tool, the specimen support proximate the knife edge and substantially stationary during the sectioning operation and loading of the thin section from the knife edge onto the specimen support.

8. The method as in claim 7, wherein the micromanipulator comprises a receptacle, and the tool comprises a forceps received by the receptacle.

9. The method as in claim 8, wherein the forceps is elongated and has a tip that is bent with respect to a longitudinal dimension of the forceps.

10. The method as in claim 9, wherein the positioning step comprises retaining the tool in the micromanipulator so that the forceps is rotatable about an axis along the longitudinal dimension.

11. The method as in claim 7, further comprising the step of, following the maintaining step and when the transfer container is disposed in the working space, controlling the tool by the micromanipulator to deposit the specimen support in a said receiving opening.

12. The method as in claim 11, further comprising the steps of, following the controlling step, removing the tool from the working space and securing a second said specimen support by the tool outside the working space.

* * * * *